United States Patent [19]

Eaton et al.

[11] Patent Number: 4,719,180

[45] Date of Patent: Jan. 12, 1988

[54] SYNTHETIC UROGASTRONE GENE, CORRESPONDING PLASMID RECOMBINANTS, TRANSFORMED CELLS, PRODUCTION THEREOF AND URGASTRONE EXPRESSION

[75] Inventors: Michael A. W. Eaton, Bledlow; Michael T. Doel, Studley Green; Norman H. Carey, Chinnor; John C. Smith, High Wycombe; David M. J. Lilley, Downley; Leslie D. Bell, Thame, all of England

[73] Assignee: G. D. Searle & Co., Skokie, Ill.

[21] Appl. No.: 649,885

[22] Filed: Sep. 13, 1984

Related U.S. Application Data

[63] Continuation of Ser. No. 289,596, Aug. 3, 1981, abandoned.

[30] Foreign Application Priority Data

Aug. 5, 1980 [GB] United Kingdom ................ 8025440

[51] Int. Cl.$^4$ ...................... C12N 1/00; C12N 15/00; C12N 1/20; C12P 21/02; C12P 21/04; C12P 19/34; C07H 21/04
[52] U.S. Cl. ........................ 435/320; 435/70; 435/71; 435/91; 435/172.3; 435/25.3; 536/27; 935/13; 935/16; 935/17; 935/29; 935/73
[58] Field of Search .................. 435/68, 70, 71, 91, 435/253, 172.3, 317; 536/27; 935/13, 16, 17, 29, 72–75

[56] References Cited

U.S. PATENT DOCUMENTS

| | | | |
|---|---|---|---|
| 4,293,652 | 10/1981 | Cohen | 435/172.3 |
| 4,322,499 | 3/1982 | Baxter et al. | 435/317 |
| 4,342,832 | 8/1982 | Goeddel et al. | 435/172.3 |

OTHER PUBLICATIONS

Itakura et al., "Expression in Escherichi coli of a Chemically Synthesized Gene for the Hormone Somatostatin", Science 196: 1056 (1977).
Lewin, "Gene Expression, vol. 2, (1974), John Wiley & Sons, London, pp. 148–156.

*Primary Examiner*—James Martinell
*Attorney, Agent, or Firm*—Timothy J. Keane; Paul D. Matukaitis; Albert Tockman

[57] ABSTRACT

A synthetic gene characterised in that it codes for the expression of urogastrone or a sub-unit thereof is disclosed.

The production thereof by the assembly and ligation of a number of nucleotide blocks is also disclosed, as are corresponding plasmid recombinants, transformed cells and the production thereof.

The expression of urogastrone is further disclosed.

Urogastrone is a polypeptide hormore (protein) which may be isolated in small amounts from human urine. It has an application in the treatment of ulcers and in the promotion of wound healing. The present invention provides a more viable commercial production.

1 Claim, 10 Drawing Figures

```
                                      -10                            -5
           Met Gln Thr Gln Lys Pro Thr Pro Ser Ser Lys
 coding   A T G C A A A C A C A A A A A C C G A C T C C A A G C T C C A A G Non-coding                                                              T T C 1                      5
           Leu Lys Lys Asn Ser Asp Ser Glu Cys Pro Leu
          C T T A A A A G A A T T C C G A T A G C G A G T G T C C T C T G

G A A T T T T C T T A A G G C T A T C G C T C A C A G G A G A C 10                          15
           Ser His Asp Gly Tyr Cys Leu His Asp Gly Val
          A G T C A C G A T G G T T A C T G T C T A C A T G A C G G C G T C

T C A G T G C T A C C A A T G A C A G A T G T A C T G C C G C A G 20                    25                          30
           Cys Met Tyr Ile Glu Ala Leu Asp Lys Tyr Ala
          T G T A T G T A T A T T G A G G C T C T A G A C A A G T A C G C G

A C A T A C A T A T A A C T C C G A G A T C T G T T C A T G C G C
```

Fig.1 (Part 1 of 2)

```
                    35                              40
 Cys Asn Cys Val   Val  Gly  Tyr  Ile Gly  Glu  Arg
 TGTAATTGCGTTGTTGGCTACATCGGTGAGCGC

ACATTAACGCAACAACCGATGTAGCCACTCGCG

Cys Gln Tyr Arg Asp Leu Lys Trp Trp Glu Leu
 TGTCAGTATCGAGATCTGAAATGGTGGGAACTT

ACAGTCATAGCTCTAGACTTTACCACCCTTGAA

55
 Arg Ter Gly Ser
 AGATAAGGATCC coding

TCTATTCCTAGG Non-coding
```

Fig.1 (Part 2 of 2)

```
                                                              HindIII
                                    -10                    -5  AluI
         Met  Gln  Thr  Gln  Lys  Pro  Thr  Pro  Ser  Ser  Lys
         ATG CAA ACA CAA AAC CGA CTC CAA GCT CCA AG
                                                    *I***
                                                       ***I T T C
                                                    ****
                                                       ***I EcoRI                         MnlI
                      1                        5
         Leu  Lys  Lys  Asn  Ser  Asp  Ser  Glu  Cys  Pro  Leu
         CTT AAA AGA ATT CCG ATA GCG AGT GTC CTC TG
         *****      *I*********              ******  *
         ***

GAA TTT TCT TAA GGC TAT CGC TCA CAG GAG AC
         ***I*      ************I*              *******  *
         ***

HinfI                      AccI                      HgaI
                 10                    15
         Ser  His  Asp  Gly  Tyr  Cys  Leu  His  Asp  Gly  Val
         AGT CAC GAT GGT TAC TGT CTA CAT GAC GGC GTC
         *****              *I*******        ++++++++

TCA CTG CTA CCA ATG ACA GAT GTA CTG CCG CAG
         *****I*              *******I***  HgaI   ++++++++

MnlI    XbaI                     FnuDII
         20                 25                       30
         Cys  Met  Tyr  Ile  Glu  Ala  Leu  Asp  Lys  Tyr  Ala
         TGT ATG TAT ATT GAG GCT CTA GAC AAG TAC GCG
                             ******    *I*********        ******

ACA TAC ATA TAA CTC CGA GAT CTG TTC ATG CGC
                             ****    ******I*        *I*
                                                          HhaI
```

Fig. 2 (Part 1 of 2)

```
                                           HphI      HaeII
                         35                      40
Cys  Asn  Cys  Val  Val  Gly  Tyr  Ile  Gly  Glu  Arg
T G T A A T T G C G T T G T T G G C T A C A T C G G T G A G C G C
                                 +++++++++ *****I*
                                          *******I

A C A T T A A C G C A A C A A C C G A T G T A G C C A C T C G C G
                                 +++++++++ *I*****
                                          *I*******

MboI
          TaqI        BglII
              45                        50
Cys  Gln  Tyr  Arg  Asp  Leu  Lys  Trp  Trp  Glu  Leu
T G T C+A G T A T C G A G A T C T G A A A T G G T G G G A A C T T
      *I*****I*******
        *I*********
·*

A C A+G T C A T A G C T C T A G A C T T T A C C A C C C T T G A A
    HphI       *****I* ********I
·*              *********I*

BamHI
             MboI
Arg  Ter  Gly  Ser
A G A T A A G G A T C C
        *I*********
         I*******

T C T A T T C C T A G G
    **********I*
             ******I
```

Fig. 2 (Part 2 of 2)

coding A G
I---

Non-coding -··-

```
              1                           5
     Leu  Lys  Lys  Asn  Ser  Asp  Ser  Glu  Cys  Pro  Leu
     C T T A A A A A G A A T T C C G A T A G C G A G T G T C C T C T G
     ------------------I------------------------------------I-------
           I (13)                              III (18)

--·-A T T T T T C T T A A G G C T A T C G C T C A C A G G A G A C
     I---------------------------I----------------------------------
               II (15)                          IV (18)

10                          15
       Ser  His  Asp  Gly  Tyr  Cys  Leu  His  Asp  Gly  Val
     A G T C A C G A T G G T T A C T G T C T A C A T G A C G G C G T C
     ----------------------------I-----------------------------------I-
                    V (18)                       VII (18)

T C A G T G C T A C C A A T G A C A G A T G T A C T G C C G C A G
     ---I------------------------------I-----------------------------
              VI (18)                          VIII (18)

20                    25                        30
       Cys  Met  Tyr  Ile  Glu  Ala  Leu  Asp  Lys  Tyr  Ala
     T G T A T G T A T A T T G A G G C T C T A G A C A A G T A C G C G
     ----------------------I------------------I
            IX (12)              XI (12)    I------------------------
                                                       XIII (18)

A C A T A C A T A T A A C T C C G A G A T C T G T T C A T G C G C
     ---------I----------------------------------I
                      X (18)                      I----------------------
                                                         XII (20)
```

Fig. 3 (Part 1 of 2)

```
                              35                              40
    Cys  Asn  Cys  Val  Val  Gly  Tyr  Ile  Gly  Glu  Arg
    T G T A A T T G C G T T G T T G G C T A C A T C G G T G A G C G C
    -----I--------------------------I-------------------------I-
             XV (16)                      XVII (13)

A C A T T A A C G C A A C A A C C G A T G T A G C C A C T C G C G
    -----------------I-----------------------------------I---------
         XII (20)              XIV (16)                 XVI (12)

45                              50
    Cys  Gln  Tyr  Arg  Asp  Leu  Lys  Trp  Trp  Glu  Leu
    T G T C A G T A T C G A G A T C T G A A A T G G T G G G A A C T T
    --------------------------I-----------------------I-------------
              XIX (15)                  XXI (12)              XXIII (14)

A C A G T C A T A G C T C T A G A C T T T A C C A C C C T T G A A
    --------I----------------------------I---------------------------I-
            XVIII (14)                   XX (14)
```

```
Arg  Ter
A G A T A A G     Coding
--------------I
XXIII (14)

T C T A T T C C T A G    Non-coding
--------------------
    XXII (12)
```

Fig. 3 (Part 2 of 2)

coding A G
|---

Non-coding -·-

```
         1                              5
  Leu  Lys  Lys  Asn  Ser  Asp  Ser  Glu  Cys  Pro  Leu
  C T T A A A A A G A A T T C C G A T A G C G A G T G T C C T C T G
  ------------------|-------------------------------|-------
         I (13)                    III (18)

---·A T T T T T C T T A A G G C T A T C G C T C A C A G G A G A C
  |----------------------------|--------------------------------
              II (15)                      IV (18)

10                             15
   Ser  His  Asp  Gly  Tyr  Cys  Leu  His  Asp  Gly  Val
   A G T C A C G A T G G T T A C T G T C T A C A T G A C G G T G T C
   -----------------------|-------------------------------|-
              V (18)                    VII*(18)

T C A G T G C T A C C A A T G A C A G A T G T A C T G C C A C A G
   ---|-----------------------------|---------------------------
           VI (18)                          VIII*(18)

20                        25                           30
     Cys  Met  Tyr  Ile  Glu  Ala  Leu  Asp  Lys  Tyr  Ala
     T G T A T G T A T A T C G A A G C T C T A G A C A A G T A C G C G
     ------------------|----------------------|
            IX (12)              XI*(12)      |--------------------
                                                     XIII (18)

A C A T A C A T A T A G C T T C G A G A T C T G T T C A T G C G C
      ----------|-----------------------------|
                      X* (18)                 |--------------------
                                                     XII (20)
```

Fig. 4 (Part 1 of 2)

```
                              35                              40
       Cys  Asn  Cys  Val  Val  Gly  Tyr  Ile  Gly  Glu  Arg
       TGTAATTGCGTTGTTGGCTACATCGGTGAGCGC
       -----I---------------------------I------------------------I-
            XV (16)                          XVII (13)

ACATTAACGCAACAACCGATGTAGCCACTCGCG
       ------------------I-----------------------------I---------
           XII (20)              XIV (16)                XVI (12)

45                              50
       Cys  Gln  Tyr  Arg  Asp  Leu  Lys  Trp  Trp  Glu  Leu
       TGTCAGTATCGAGATCTGAAATGGTGGGAACTT
       ------------------------I------------------------I--------------
            XIX (15)                  XXI (12)                XXIII (14)

ACAGTCATAGCTCTAGACTTTACCACCCTTGAA
       -------I----------------------------I----------------------------I-
              XVIII (14)                     XX (14)
```

```
Arg  Ter
AGATAAG        Coding
-------------I
XXIII (14)

TCTATTCCTAG    Non-coding
--------------------
  XXII (12)
```

Fig. 4 (Part 2 of 2)

Fig. 8 (Part 1 of 2)

SYNTHETIC UROGASTRONE GENE, CORRESPONDING PLASMID RECOMBINANTS, TRANSFORMED CELLS, PRODUCTION THEREOF AND UROGASTRONE EXPRESSION

This is a continuation of application Ser. No. 06/289,596, filed Aug. 3, 1981 now abandoned.

This invention relates to a synthetic urogastrone gene, to corresponding plasmid recombinants and transformed cells, to the production thereof and to urogastrone expression.

BRIEF DESCRIPTION OF THE DRAWINGS

FIG. 1 Urogastrone coding sequence
FIG. 2 Restriction enzyme sites on Urogastrone coding sequence
FIG. 3 Illustration of oligonucleotide block
FIG. 4 Modified sequence block
FIG. 5 Block assembly sequence
FIG. 6 Condensation reaction sequence
FIG. 7 Chemical scheme for removing blocking groups
FIG. 8 Preparation of two general segments
FIG. 9 Preparing pLF1 plasmid
FIG. 10 Preparing pUrI plasmid Urogastrone is a polypeptide hormone (protein) synthesised in the duodenum and in the salivary glands of normal humans, (see, for example, Heitz, et al, (1978), Gut, 19, 408–413). Urogastrone suppresses the secretion of gastric acid and promotes cell growth, (see, for example, Elder, et al, (1975), Gut, 16, 887–893). Therefore, it has an application in the treatment of ulcers and in the promotion of wound healing. Urogastrone is excreted in small aounts in human urine and may be isolated therefrom. There exists, however, a need for a more viable commercial production thereof and such is provided according to the present invention.

Figure 5:
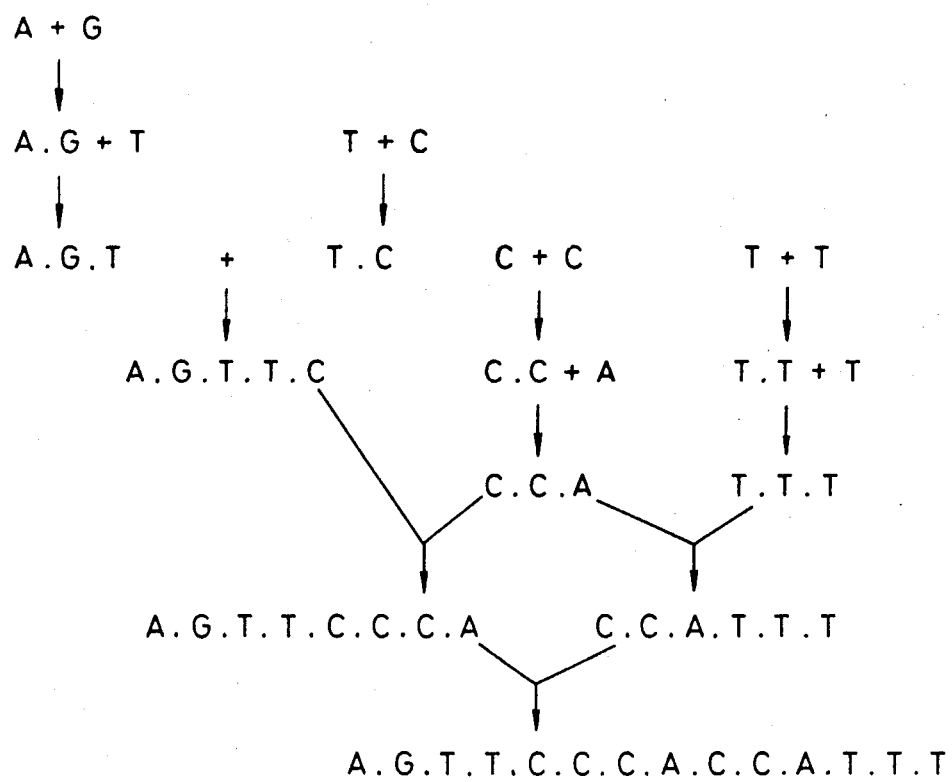

Urogastrone is known to consist of 53 amino acids in the following sequence:

Asn Ser Asp Ser Glu Cys Pro Leu Ser His Asp—
　　Gly Tyr Cys Leu His Asp Gly Val Cys Met Tyr—
　　Ile Glu Ala Leu Asp Lys Tyr Ala Cys Asn Cys—
　　Val Val Gly Tyr Ile Gly Glu Arg Cys Gln Tyr—
　　　　　Arg Asp Leu Lys Trp Trp Glu Leu Arg (see, for example, Gregory H., and Preston, B. M., (1977), Int. J. Peptide Protein Res., 9, 107–118.)

From the above amino acid sequence, a corresponding synthetic gene sequence has been invented, subject to a number of specific non-obvious criteria, and oligonucleotide blocks synthesised which, when assembled, form a synthetic gene coding for urogastrone. The blocks have been hybridised and ligated in pre-determined stages to construct the urogastrone gene in two portions. These have been cloned in two operations into a new specifically-designed chimeric E. coli/S. aureus vector so as to produce a full length urogastrone gene flanked only by E. coli plasmid DNA. The gene has been excised from this recombinant and re-cloned into vectors specifically designed to maximise expression of the gene in E. coli, under the control of the promoter obtained from the E. coli tryptophan operon. A protein resembling human urogastrone has thus been expressed in E. coli.

From the above amino acid sequence, because of the degeneracy of the genetic code, it is possible to predict numerous nucleotide sequences which would code for the protein.

In the inventive determination of an optimum sequence from the large number of possibilities, several non-obvious criteria have been observed. Firstly, trinucleotide codons should be used which are acceptable or preferable in the cells to be used, in particular E. coli. Secondly, it was decided that it was desirable to have different restriction enzyme recognition sites at the termini of the molecule so as to allow insertion into a plasmid in a desired orientation. Moreover, it was decided to select sites which allowed the use of well-understood cloning vectors, such as pBR322 (see, for example, Bolivar, F., et al, (1977), Gene, 2, 95–113). In fact, Hind III and Bam HI sites were selected and introduced at the 5' and 3' ends, respectively. Thirdly, it was thought desirable to introduce a series of restriction endonuclease recognition sites strategically placed along the molecule to enable the gene to be specifically dissected to aid characterisation and, possibly mutagenesis. Also, this measure allowed the two portions of the molecule to be cloned in stages. In particular, an Xba I site was introduced at a central location in the gene. Fourthly, the synthesis should not be unnecessarily complicated and illegitimate cross-hybridisations should be minimised in order to facilitate gene assembly. Using a computer, energies of interactions arising from all possible approximations were calculated (see, for example, Tinoco, Jr., I., et al, (1971), Nature, 230, 362–367; Powers, G. J., et al, (1975), JACS, 97, 875–889), so that stable off-diagonal interactions might be avoided where possible. Fifthly, since the protein ultimately expressed in bacterial cells will be in the form of a fusion product, it was desirable to have a means of cleaving the urogastrone portion from such a fusion product. Since urogastrone is known to be insensitive to trypsin (see, for example, Gregory and Preson, loc cit), the codons specifying the dipeptide lys-lys were introduced near the end of the gene corresponding to the urogastrone N-terminus in order to serve as a substrate for tryptic proteolysis.

The present invention relates to a synthetic gene characterized in that it codes for the expression of urogastrone or a sub-unit thereof.

The particular preferred sequence selected for the coding portion of the synthetic urogastrone gene is as follows:

```
5' A A T T C C G A T A G C G A G T G T C C T C T G—
—3' T T A A G G C T A T C G C T C A C A G G A G A C—
  —A G T C A C G A T G G T T A C T G T C T A C A T—
  —G A C G G T C A G T G C T A C C A A T G A C A G—
  —A T G T A C T G C C C G T C T G T A T G T A T A T—
  —T G A G G C T C T A G A C A G C A G A C A T A C—
  —A T A T A A C T C C G A G A T C T G T A G T A C—
  —G C G T G T A A T T G C G T T G T T G G C T A C—
  —T C A T G C G C A C A T T A A C G C A A C A A C—
  —C G A T G A T C G G T G A G C G C T G T C A G T—
  —A T C G A G A T C T T A G C C A C T C G C G A C—
  —A G T C A T A G C T C T A G A G A A A T G G T G—
  —G G A A C T T A G A C T T T A C C A C C C T T G—
                                      —A A T C T
```

One aspect of the present invention is directed accordingly. A sub-unit of such a sequence also constitutes an aspect of the present invention.

In fact, bearing in mind, inter alia, the above-mentioned considerations, for convenience, a slightly longer sequence was selected which is as follows:

Coding: A G C T T A A A A A G A A T T C C G A T A—
—G C G A G T—
Non-Coding: A T T T T T C T T A A G G C T A T C G—
—C T C A G T C C T C T G A G T C A C G A T G G T—
—T A C T G T C T C A G G A G A C T C A G T G C T—
—A C C A A T G A C A G A A C A T G A C G G C G T—
—C T G T A T G T A T A T T G A G T G T A C T G C—
—C G C A G A C A T A C A T A T A A C T C G C T C—
—T A G A C A A G T A C G C G T G T A A T T G C G—
—C G A G A T C T G T T C A T G C G C A C A T T A—
—A C G C T T G T T G G C T A C A T C G G T G A G—
—C G C T G T C A A A C A A C C G A T G T A G C C—
—A C T C G C G A C A G T G T A T C G A C T C T—
—G A A A T G G T G G G A A C T T C A T A G C T C—
—T A G A C T T T A C C A C C C T T G A A A G A T—
A A G T C T A T T C C T A G The whole of this expanded sequence is shown in FIG. 1 of the accompanying drawings and the restriction enzyme recognition sites are shown in FIG. 2 of the accompanying drawings.

Another aspect of the present invention is directed accordingly. A sub-unit of such a sequence also constitutes an aspect of the present invention.

In the above sequences, it is to be appreciated that minor variations are possible without departing from the present inventive concept.

The present invention also relates to a process for the production of such a synthetic gene or a sub-unit thereof characterised in that it comprises the assembly and ligation of a number of oligonucleotide blocks.

It was in fact decided to synthesise a molecule having the above expanded sequence by making 23 synthetic oligonucleotide blocks as illustrated in FIG. 3 of the accompanying drawings, which will assemble by single-strand overlaps to give the complete double-stranded nucleotide sequence.

In order to minimise strong illegitimate interactions near the centre of the molecule during assembly, certain blocks of modified sequence have also been synthesised, as illustrated in FIG. 4 of the accompanying drawings.

As mentioned above, the synthetic blocks selected are shown in FIG. 3 of the accompanying drawings. The blocks may be constructed using known synthesis techniques (see, for example, Agarwal, et al, (1970), Nature, 227, 27–34; and Crea, et al, (1978), Proc. Natl. Acad. Sci. USA, 75, 5765-5769).

The synthetic methods will now be illustrated with reference to the synthesis of the tetradecanucleotide ApGpTpTpCpCpCpApCpCpApTpTpT.

The methods of building up oligonucleotides from smaller units by successive coupling reactions are well known (see, for example, Hsiung, et al, (1979), Nucleic Acid Research, 6, 1371-1385). The completely protected tetradecanucleotide was built up as shown in FIG. 5 of the accompanying drawings (wherein, for convenience, protecting groups are not shown).

Figure 6:
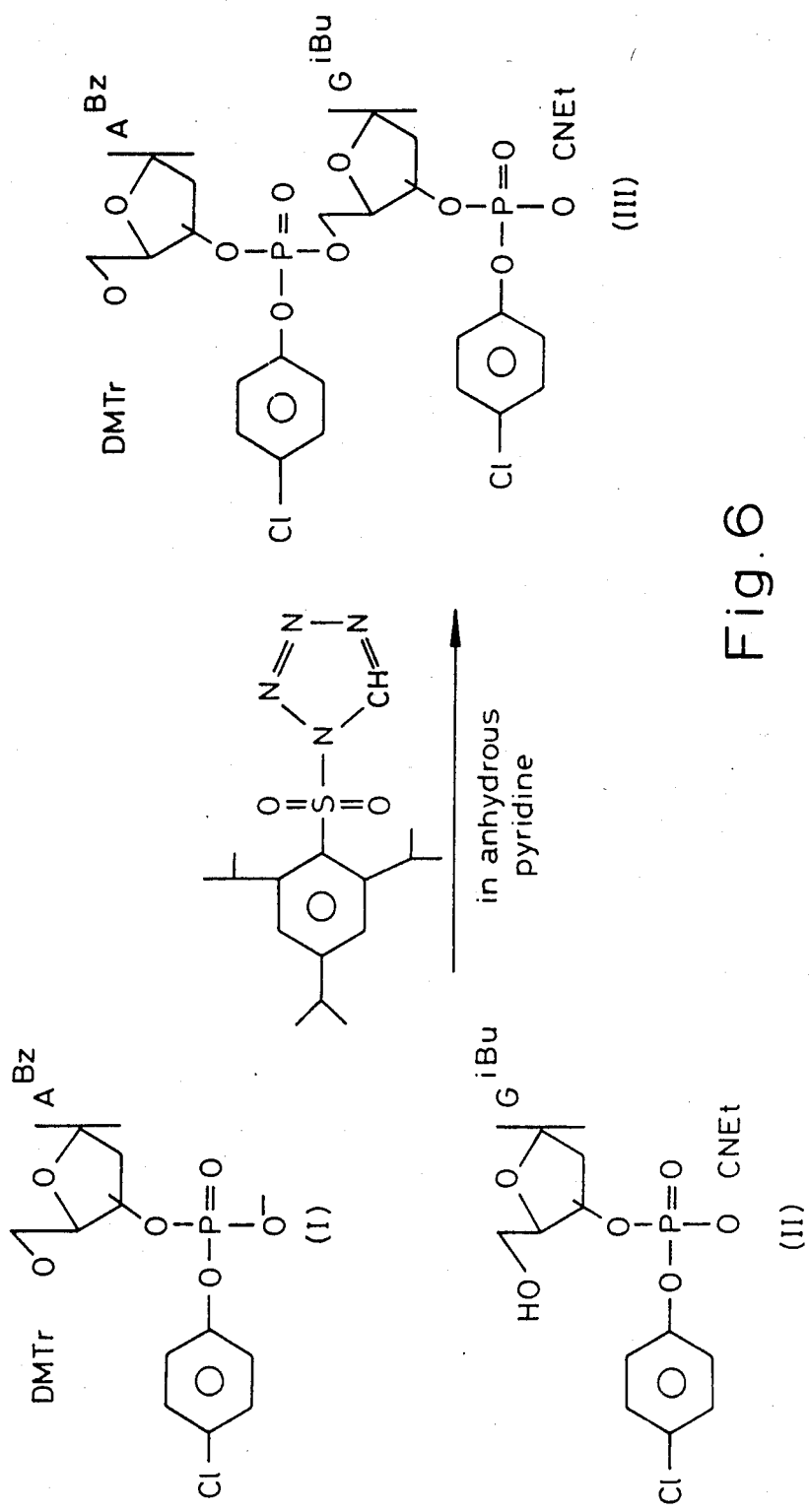

The condensation reactions indicated by arrows in FIG. 5 were carried out by the following procedure exemplified in the synthesis of:

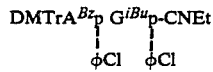

as shown in FIG. 6 of the accompanying drawings. From 1.1 to 1.5 mmole of the 3'-phosphodiester component (I) was condensed with 1.0 mmole of the 5'-hydroxyl component (II) in anhydrous pyridine in the presence of from 3 to 4.5 mmoles of 2,4,6-triisopropyl-benzene-sulphonyltetrazolide. The reaction was left for 1 hour at room temperature or until chromatography on silica TLC plates eluted with 10% (v/v) methanol in chloroform showed that the hydroxyl component was exhausted. The reaction was quenched with 5% (w/v) sodium bicarbonate solution and extracted with chloroform. The chloroform extract was dried and loaded onto a reverse phase chromatography column (ODS bonded to 15-25 micron silica). The fully protected dinucleotide product (III) was eluted with a solvent gradient from chloroform:methanol:water (2:6:3 v/v) to chloroform:methanol:water (2:6:0.5 v/v). The product (III) was extracted into chloroform and dried. The final isolated yield was 81%.

Figure 7:
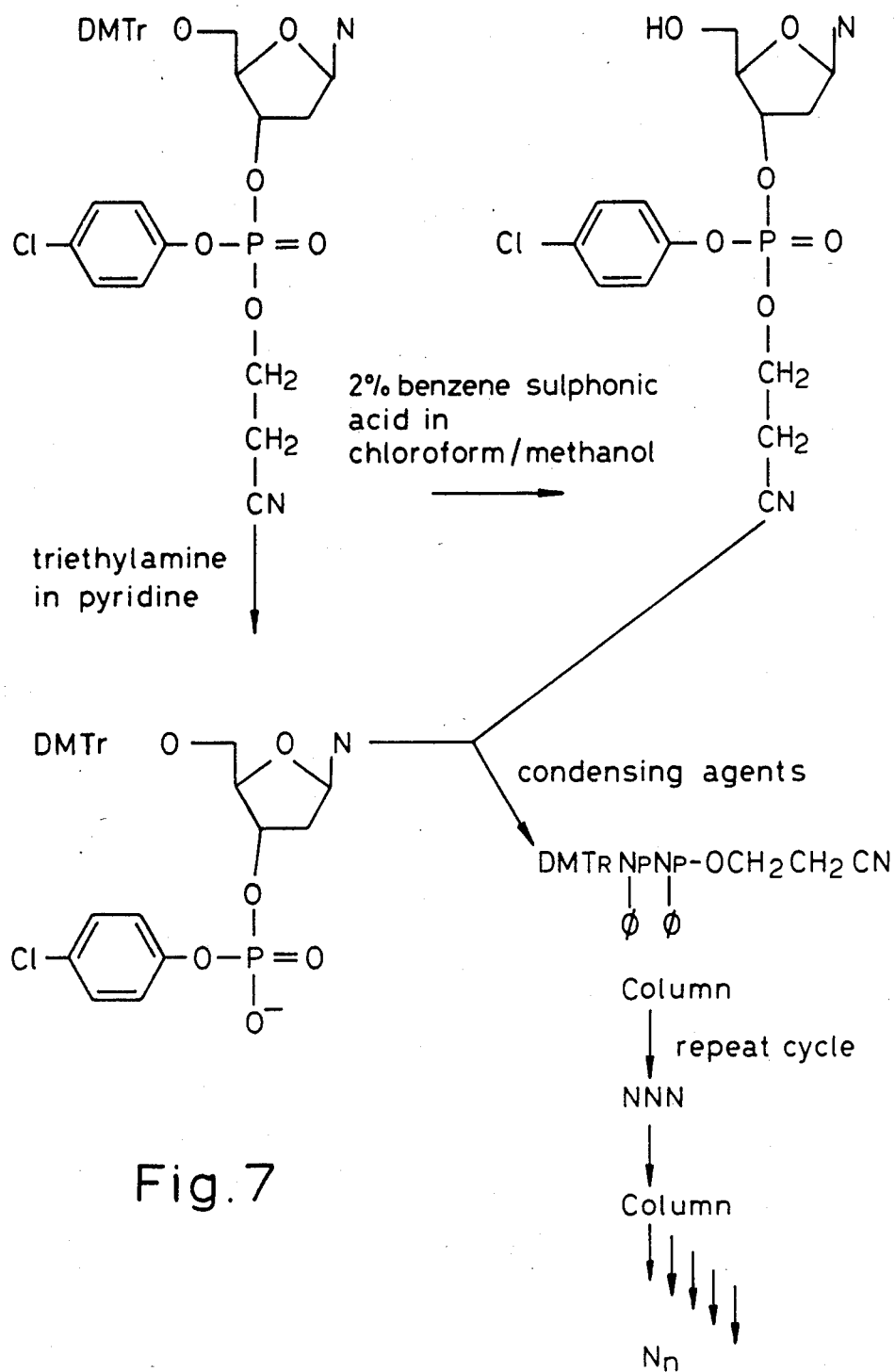

To proceed to further condensations, the terminal protecting group (DMTr or CNEt) was removed selectively using triethylamine in pyridine (CNEt) or a 2% (w/v) solution of benzene sulphonic acid in chloroform:methanol (DMTr) as shown in FIG. 7 of the accompanying drawings.

At the completion of the synthesis, all of the protecting groups were removed by sequential treatment with 0.1M tetraethylammonium fluoride in THF/pyridine/water (8:1:1 v/v), ammonia and 80% acetic acid. The deprotected oligonucleotides were purified by ion-exchange HPLC and sequence analysis was carried out by the method of Wu, et al, (1976), Anal. Biochem., 74, 73-93.

Figure 8:
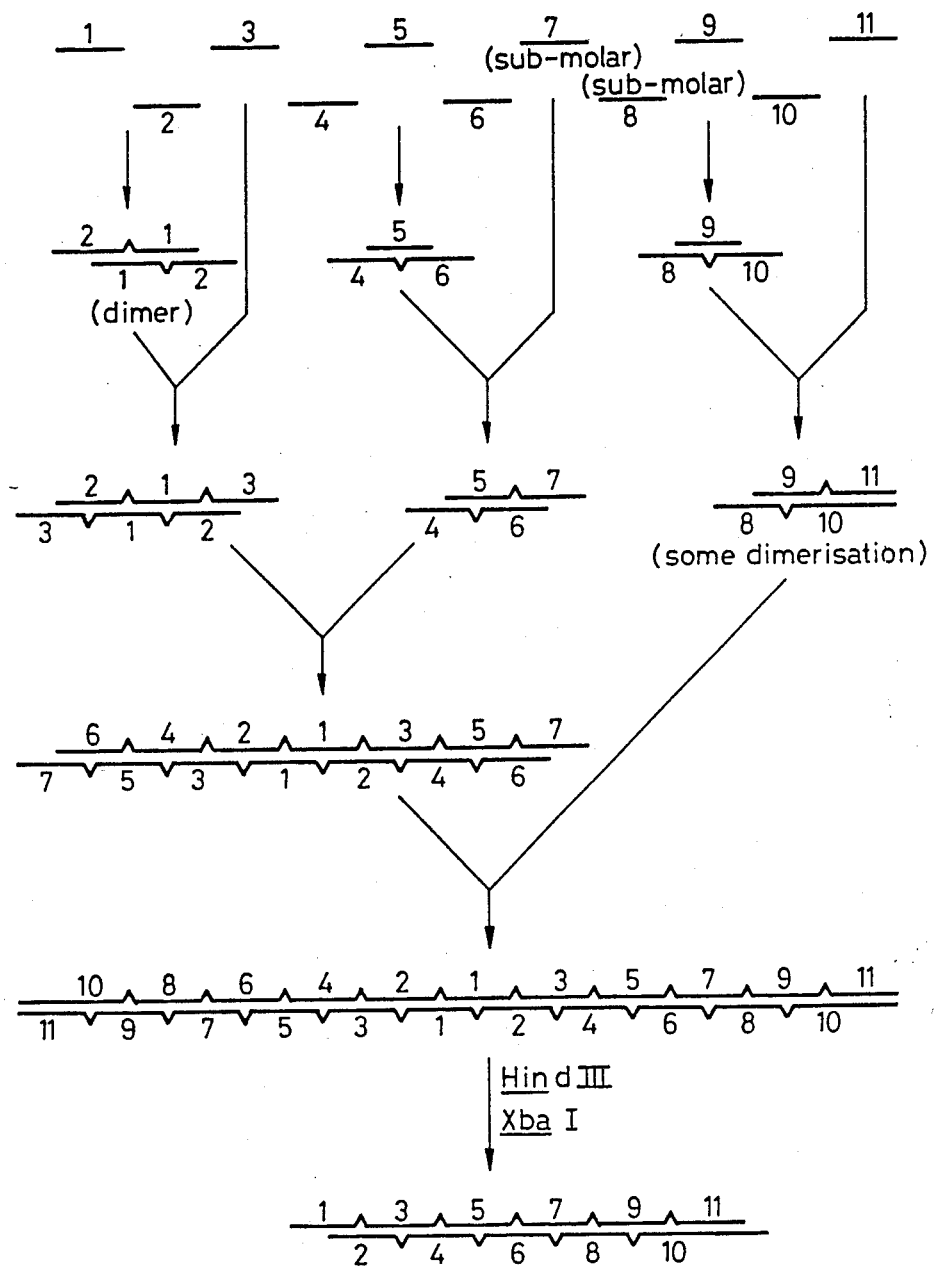

The oligomeric blocks of nucleotides were hybridised and ligated (see, for example, Agarwal, et al, loc cit) in a series of steps, in order to minimise the possibilities for undesirable interactions, leading to the formation of the two portions as shown in FIG. 8 of the accompanying drawings. The order of the additions in the assembly scheme was optimised for minimal incorrect ligations and in the case of especially difficult oligomeric blocks, notably 7 and 8, sub-molar quantities were used in order to remove all monomeric units before further additions were made.

In more detail:

Left-hand portion: Blocks 1 and 2 were ligated to form a dimer about the Hind III site. Blocks 4, 5 and 6 and 8, 9 and 10 were also ligated in the first round of the assembly scheme. Molar equivalents were used for all but block 8 where 0.75 molar equivalents were employed.

Block 3 were ligated with 1+2, block 7 (0.75 molar equivalent) with 4 to 6 and block 11 with 8 to 10. The 8+9+10+11 assembly has one flush end, hence some blunt-end dimerisation was observed.

1 to 3 and 4 to 7 were ligated and finally 8 to 11 were ligated to the resulting 1 to 7 species.

The dimeric 1 to 11 left-hand portion was then cleaved by Hind III (EC 3.1.23.21) and Xba I (EC 3.1.23.4) to generate the monomeric left-hand portion, with the correct cohesive termini to allow construction of recombinant plasmids.

Right-hand portion: Blocks 12 and 13 were ligated to form a dimer about the Xba I site and blocks 20, 23 and 22 similarly ligated to form a dimer about the Bam HI site. Blocks 14, 15 and 17, and 16, 18 and 19 were also ligated at this stage.

The 12, 13 dimer and the 14, 15, 17 assembly were ligated, as were the 16, 18, 19 assembly with the 20, 22, 23 dimer, where block 21 was used as a joining section.

These two species were then ligated to give an oligomeric molecule which was cleaved by Xba I and Bam HI (EC 3.1.23.6) to give the monomer 12 to 13 species having the correct cohesive termini to allow construction of recombinant plasmids.

The present invention further relates to a plasmid recombinant characterised in that it comprises a plasmid vector having inserted therein at an appropriate insertion site such a synthetic gene or a sub-unit thereof, the plasmid recombinant enabling translation in the correct phase for the mRNA corresponding to the inserted gene or sub-unit thereof and having a bacterial promoter upstream of and adjacent to the insertion site such that the inserted gene or sub-unit thereof is under bacterial promoter control.

A particular vector, designated pLF1, has been specifically designed to afford advantages for the purposes of the present invention. The inventive plasmid, pLF1, is a 5K bp plasmid which may be propagated in *E. coli* and which may be constructed from PAT153 and pUB110 (see, for example, Gryczan, T. J., et al, (1978), J. Bacteriol., 134, 318) by inserting the DNA sequence of the *S. aureus* plasmid pUB110 between the EcoRI and Bam HI sites thereof (comprising approximately 870 bp) between the EcoRI and Bam HI sites of PAT153, thereby replacing that region of PAT153.

The present invention further relates to a process for the production of such a plasmid recombinant characterised in that it comprises inserting such a synthetic gene or a sub-unit thereof into an appropriate insertion site of an appropriate plasmid vector.

The following illustrates the present invention:

Phosphorylation of oligonucleotide blocks: In each case, 6 μg of oligomer and 60 μCi of [γ-$^{32}$P] ATP (>5000 Ci/mMol) were dried and redissolved in a final buffer concentration of 50 mM Tris-HCl, pH 7.8, 10 mM MgCl$_2$, 0.25 mM ATP, 10 mM β-mercaptoethanol and incubated with 4 units (1 unit is the amount that catalyses the production of 1 n mole of acid-insoluble $^{32}$P after incubation for 30 minutes at 37° C. according to Richardson, C. C., (1972), Progress in Nucleic Acids Research, 2, 815) of T4 polynucleotide kinase (EC 2.7.1.78, Bethesda Research Labs) at 37° C. for 15 minutes. The enzyme was subsequently inactivated by a 5 minute incubation at 100° C.

Ligation of oligonucleotide blocks: Except where indicated above, equimolar quantities (6 to 18 μg) of oligonucleotide blocks were incubated in 50 mM Tris-HCl, pH 7.8, 10 mM MgCl$_2$, 1 mM ATP, 20 mM dithiothreitol (DTT) with 6 units (1 unit is the amount that catalyses the conversion of 1 n mole of $^{32}$PPi into (α/β$^{32}$P)-ATP in 20 minutes at 37° C. according to Weiss, B., et al, (1968), J. Biol. Chem., 243, 4543) of T4 DNA ligase (EC 6.5.1.1, Bethesda Research Labs) at 25° C. for from 3 to 16 hours. Ligated DNA was precipitated by addition of 2.5 vol absolute ethanol, collected by centrifugation and redissolved in water.

Purification of ligated species: Ligated oligonucleotide blocks were electrophoresed on 20% (w/v) polyacrylamide in 90 mM Tris-HCl, pH 8.3, 90 mM boric acid, 2.5 mM EDTA (TBE buffer), and the fragments located by autoradiography. Slices of gel containing the fragments were excised and the DNA electroeluted at 1 mA in TBE buffer onto 0.5 ml of DEAE cellulose (DE52, Whatman) for a few hours. After extensive washing by 0.1M NH$_4$OAc, 2 mM Mg(OAc)$_2$, 0.02% (w/v) SDS, 0.02 mM EDTA (AGEB buffer), the DNA was eluted from the DEAE cellulose by 2 ml of 1.1M NaCl in AGEB buffer and precipitated by addition of 2.5 vol. absolute ethanol.

Figure 9:
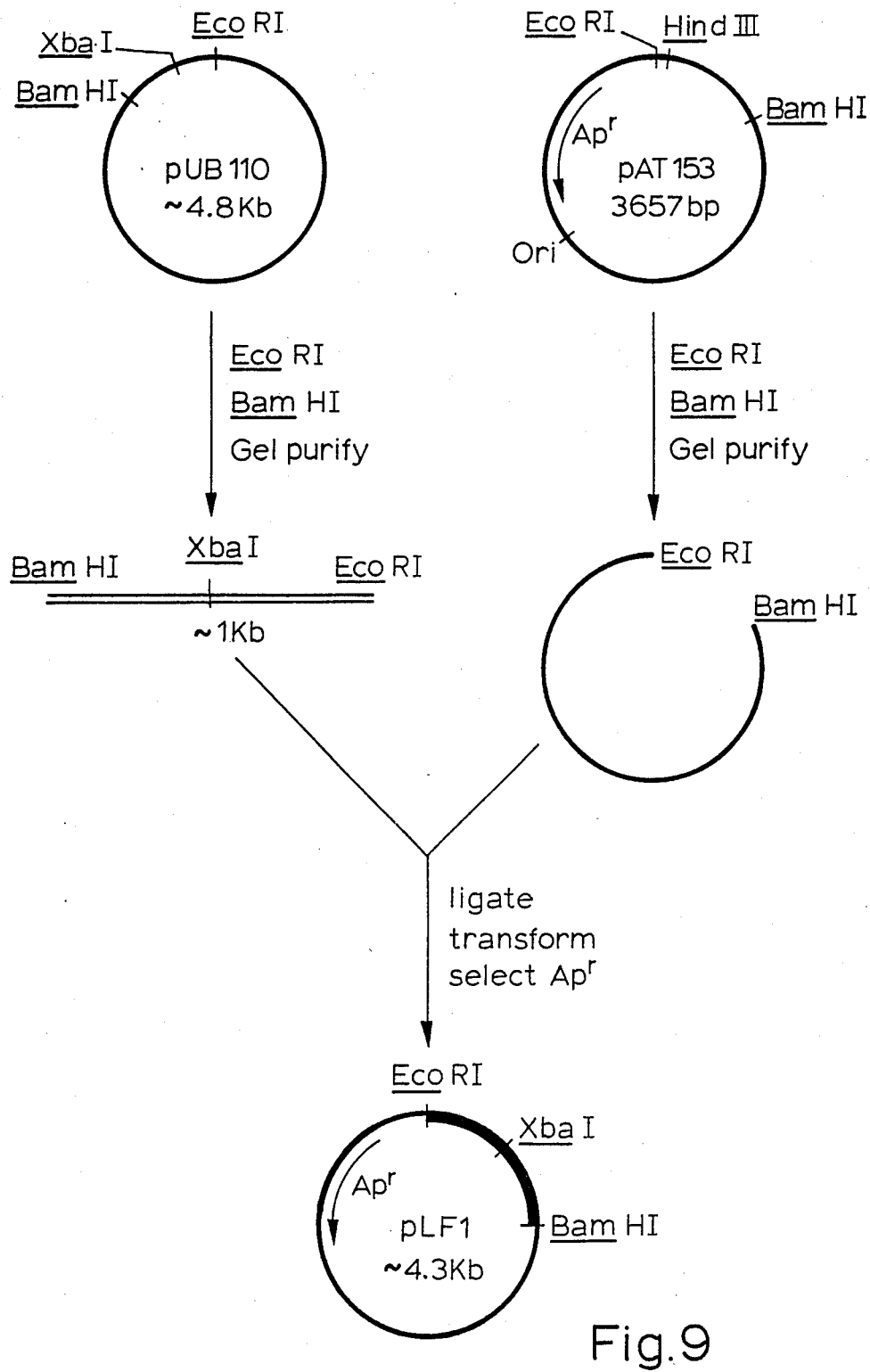

Construction of chimeric cloning vector pLF1: In order to facilitate the two-stage cloning of urogastrone, it was desirable to construct a vector or vectors having Hind III, Xba I and Bam HI cleavage sites, see FIG. 9 of the accompanying drawings. However, no readily available *E. coli* plasmids possess Xba I sites. It was surprisingly noticed that the *S aureus* plasmid pUB110, which cannot be propagated in *E. coli* (see, for example, Keggins, K. M., et al (1978), Proc. Natl. Acad. Sci. U.S.A., 75, 1423), contains a region of about 1kbp of DNA bounded by sites for EcoRi and Bam HI having an approximately central Xba I site. Therefore, pUB110 was cleaved with EcoRI (EC 3.1.4.32) and Bam HI and the DNA fragments electrophoresed on 5% (w/v) polyacrylamide. The approximately 1 kbp EcoRI/Bam HI fragment was removed by electroelution from the excised gel slice onto DEAE cellulose, eluted by 1.1M NaCl and ethanol precipitated. The *E. coli* plasmid pAT153 (see, for example, Twigg, A. J., and Sherratt, D., (1980), Nature, 283, 216-218) was also cleaved with EcoRI and Bam HI, and the 3282 bp fragment purified by electroelution as above. These two purified DNA fragments were ligated in equimolar quantities using 10 units of T4 DNA ligase in 50 mM Tris —HCl, pH 7.8, 10 mM MgCl$_2$, 1 mM ATP, 20 mM DTT at 15° C. for 18 hours. After ethanol precipitation, the ligated DNA was dissolved in 100 μl 10 mM Tris pH 7.5, 10 mM MgCl$_2$, 10 mM CaCl$_2$ and transformed into *E. coli* K12 HB101 (genotype gal$^-$, lac$^-$, ara$^-$, pro$^-$, arg$^-$, str$^r$, rec A$^-$,r$_k$$^-$, M$_k$$^-$; see, for example, Boyer, H. W., and Roullard-Dussoix, D., J. Mol. Biol., 41, 459-472) using known methods (see, for example, Cohen, et al, (1972), Proc. Natl. Acad. Sci. U.S.A., 69, 2110-2114) and transformants resistant to 100 μg/ml ampicillin selected. Several transformants were analysed further by restriction enzyme cleavage of plasmid DNA, and one full length clone, designated pLF1, selected for further use as a cloning vector. At a later stage, an additional Hind III restriction sequence was created at the EcoRI site.

Figure 10:
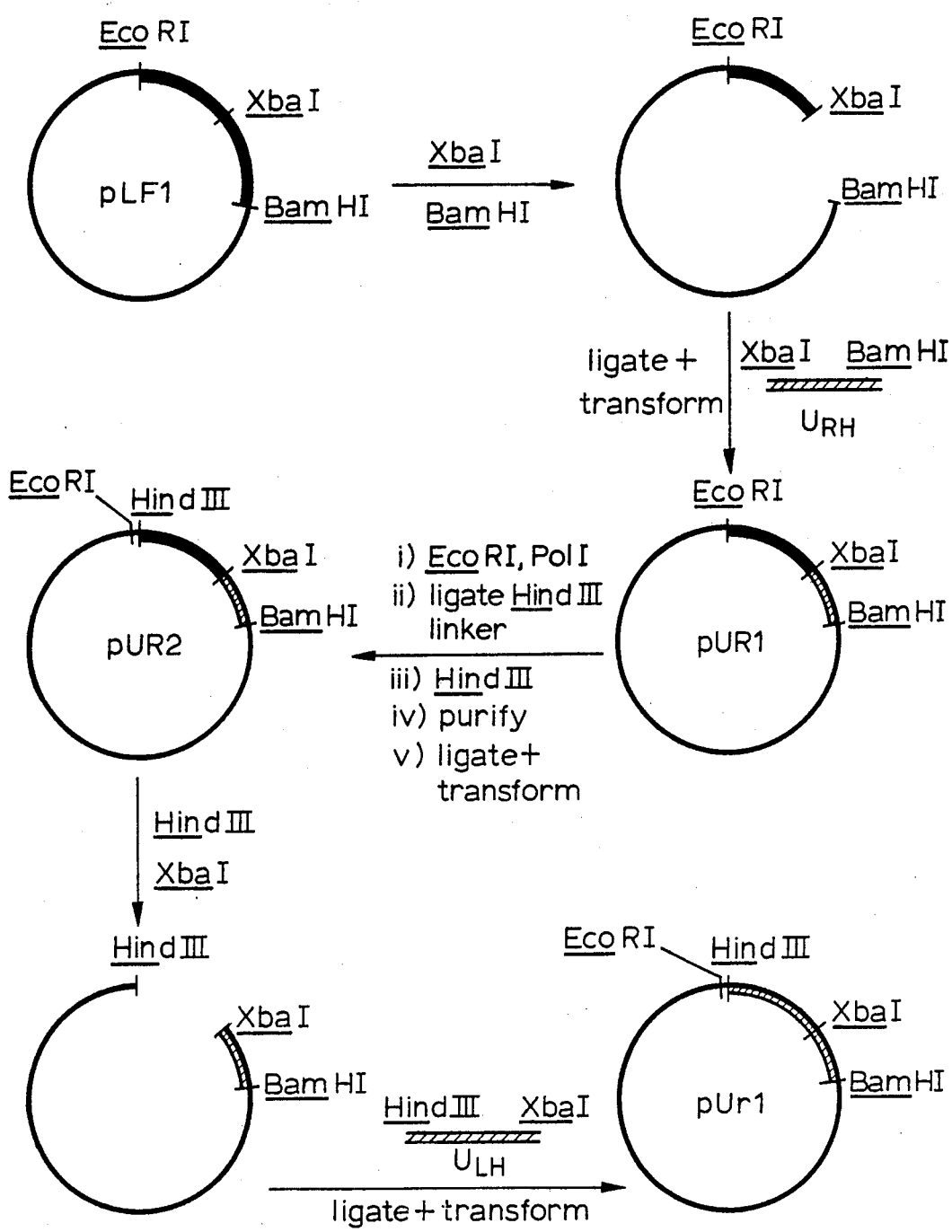

Cloning of the synthetic urogastrone gene in pLF1: The two portions of the assembled urogastrone gene were cloned in two transformation stages, as illustrated in FIG. 10 of the accompanying drawings.

Right-hand portion: The longer fragment of Xba I, Bam HI-cleaved pLF1 was purified by electroelution as above and ligated to a large excess of the right-hand portion assembly of the urogastrone gene using 10 units T4 DNA ligase in 50 mM Tris-HCl, pH 7.8, 10 mM MgCl$_2$, 1 mM ATP, 20 mM DTT at 15° C. for 18 hours. This was transformed into *E. coli* as before, with selection for 100 μg/ml ampicillin. Several transformants were selected for plasmid analysis by restriction enzyme cleavage analysis and one clone, designated pUR1, used for further cloning. The sequence of the inserted urogastrone gene DNA was confirmed by chemical degradation analysis (see, for example, Maxam, A., and Gilbert, W., (1977), Proc. Natl. Acad. Sci. U.S.A., 74, 560-4).

In order to have a Hind III site for ligation to the 5' end of the left-hand portion of the gene, the EcoRI site was modified as follows: pUR1 was cleaved with EcoRI and the resulting recessed ends filled using 5 units (1 unit is the amount that incorporates 10 n moles of total nucleotides into an acid-precipitable fraction in 30 minutes at 37° C. using poly-d(A-T) as primer according to Richardson, C. C., et al, (1964), J. Biol. Chem., 239, 222) of DNA polymerase I (EC 2.7.7.7) in 50 mM Tris-HCl, pH 7.5, 10 mM MgCl$_2$, 1 mM β-mercaptoethanol with 0.25 mM of each deoxynucleotide for 30 minutes at 15° C.

To the resulting flush ends, were ligated a large excess of synthetic Hind III linkers (Collaborative Research) by the known blunt end ligation procedure (see, for example, Ullrich, A., et al, (1977), Science, 196, 1313-1319). The DNA was ligated using 6 units of T4 DNA ligase in 50 mM Tris-HCl, pH 7.8, 10 mM MgCl$_2$, 1 mM ATP, 20 mM DTT at 15° C. for 18 hours.

After Hind III restriction cleavage and purification, the full length plasmid was religated and transformed into *E. coli* as above, with selection for 100 μg/ml ampicillin. A transformant having a Hind III site, designated pUR2, was selected for further cloning.

Left-hand portion: pUR2 was cleaved with Hind III and Xba I restriction enzymes and the longer fragment purified by electroelution as above. This was ligated to a two-fold molar excess of the assembled left-hand portion of the urogastrone gene using 6 units T4 DNA ligase in 50 mM Tris-HCl, pH 7.8, 10 mM MgCl$_2$, 1 mM ATP, 20 mM DTT for 18 hours at 15° C. This was transformed into *E. coli* K12 MRC 8 (genotype dap 103 hsd R met Bl glm 533 upp 1 dap 101 sup E thy A 103 deo rec Al) with selection for 100 μg/ml ampicillin. Several transformants were selected for plasmid analysis by restriction enzyme cleavage. One clone, designated pUrI was used for further characterisation and cloning. The sequence of the full urogastrone gene was confirmed by chemical degradation analysis. It should be noted that pUrI has no remaining *S aureus* DNA sequence present.

The present invention also relates to a cell, in particular an *E. coli* cell, characterised in that it comprises inserted therein such a synthetic gene or a sub-unit thereof or such a plasmid recombinant.

The present invention further relates to a process for the production of such a cell characterised in that it comprises inserting such a synthetic gene or a sub-unit thereof or such a plasmid recombinant into a cell.

Expression of urogastrone in *E. coli:* The urogastrone gene insert was cleaved from pUrI by Hind III and Bam HI cleavage and purified by polyacrylamide gel electrophoresis and electroelution as above. This fragment was ligated to Hind III, Bam HI-cleaved pWT121 and pWT221, (see, for example, Tacon, W. C. A., et al, (1980), Molec. Gen. Genet. 177, 427) and the recombinant molecules used to transform *E. coli* MRC 8, (see, for example, Emtage, J. S., et al, (1980), Nature, 283, 171-174), with selection for 100 μg/ml ampicillin. Transformants containing full length urogastrone genes were characterised by restriction enzyme cleavage analysis and DNA was purified by isopycnic centrifugation in caesium chloride.

Expression of urogastrone-like fusion protein was induced by growth of cells in L-broth (luria broth: 1% (w/v) bacto tryptone., 0.5% (w/v) bacto yeast extract, 0.5% (w/v) NaCl, 0.2% (w/v) glucose, 0.004% (w/v) thymine, pH 7) containing 100 μg/ml ampicillin to an A600 nm of 0.3. Following centrifugation, the cells were washed and resuspended in M9 medium lacking tryptophan, but containing 20 μg/ml 3 β-indole acrylic acid. The cells were incubated at 37° C. for 4 hours. Under these conditions maximal tryptophan promoter activity is known to occur (see Tacon, et al, loc cit), and hence expression of the urogastrone fusion protein.

The present invention also relates to a process for the production of urogastrone or a sub-unit thereof characterised in that it comprises culturing such a cell and recovering expressed protein.

As mentioned above, urogastrone has an application in the treatment of ulcers, and also in other instances where the growth promoting activity thereof would be benefical, for example, in wound healing. Conventional administration forms may be used, the active material being used in an effective amount, for example from 0.1 to 1.0 μg/kg body weight, more preferably about 0.25 μg/kg body weight, optimally together with a conventional pharmaceutically-acceptable carrier, diluent or adjuvant.

We claim:

1. The plasmid pUrI.

* * * * *